United States Patent
Hein

[11] Patent Number: 5,108,361
[45] Date of Patent: Apr. 28, 1992

[54] DEVICE FOR INFLUENCING AN ORGANISM

[76] Inventor: Piet Hein, Damsbo, DK-5683 Haarby, Denmark

[21] Appl. No.: 488,001
[22] PCT Filed: Nov. 8, 1988
[86] PCT No.: PCT/DK88/00184
  § 371 Date: Jun. 4, 1990
  § 102(e) Date: Jun. 4, 1990
[87] PCT Pub. No.: WO89/04191
  PCT Pub. Date: May 18, 1989

[30] Foreign Application Priority Data
Nov. 10, 1987 [DK] Denmark .................. 5887/87

[51] Int. Cl.⁵ .............................. A61M 21/00
[52] U.S. Cl. .......................... 600/28; 600/27; 128/421
[58] Field of Search ............. 600/27, 28, 26; 128/421, 420.5, 420 A

[56] References Cited

U.S. PATENT DOCUMENTS

| 2,465,838 | 3/1949 | Bernard | 128/421 |
| 3,490,458 | 1/1970 | Allison | 128/421 |
| 4,195,626 | 4/1980 | Schweizer | 128/774 |

FOREIGN PATENT DOCUMENTS

| 0076125 | 4/1983 | European Pat. Off. | |
| 301742 | 5/1983 | PCT Int'l Appl. | |
| 1168266 | 7/1985 | U.S.S.R. | 128/421 |
| 2052994 | 2/1981 | United Kingdom | |

Primary Examiner—William E. Kamm
Assistant Examiner—Kennedy J. Schaetzle
Attorney, Agent, or Firm—Cushman, Darby & Cushman

[57] ABSTRACT

A device for influencing a human or other biological or artificial organism by exposing the organism to signals which are short pulses supplied in a plurality of temporally successive series with increasing and/or decreasing frequency. The signals are acoustic, optical, mechanical and/or electrical signals. These signals allow a stimulation of cerebral waves.

7 Claims, 5 Drawing Sheets

SUPERSINUSOIDE

DEVICE FOR INFLUENCING AN ORGANISM

TECHNICAL FIELD

The invention relates to a device for influencing a human or other biological or artificial organism by exposing the organism to signals comprising short pulses supplied in one or several series with increasing and/or decreasing frequency, the individual series being displaced in relation to each other, and the pulses of each series optionally coinciding with some of the pulses of a preceding series.

BACKGROUND ART

U.S. Pat. No. 4,195,626 discloses a supply of short pulses to the human body. The intervals between the pulses are linearly, exponentially or randomly variable.

DESCRIPTION OF THE INVENTION

In order to obtain a tranquilizing (or stimulating) effect, it is very important that the pulses are correctly intensity-modulated. According to the invention this object is achieved by intensity-modulating the pulses of each series in such a way that the pulses increase and/or decrease, and the envelope curves of two subsequent series for increasing and decreasing, respectively, overlap each other so that the transition from one series to the next is not noticeable.

BRIEF DESCRIPTION OF THE DRAWINGS

The invention is described in greater detail below with reference to the accompanying drawings, in which.

BEST MODE FOR CARRYING OUT THE INVENTION

Figure 1:
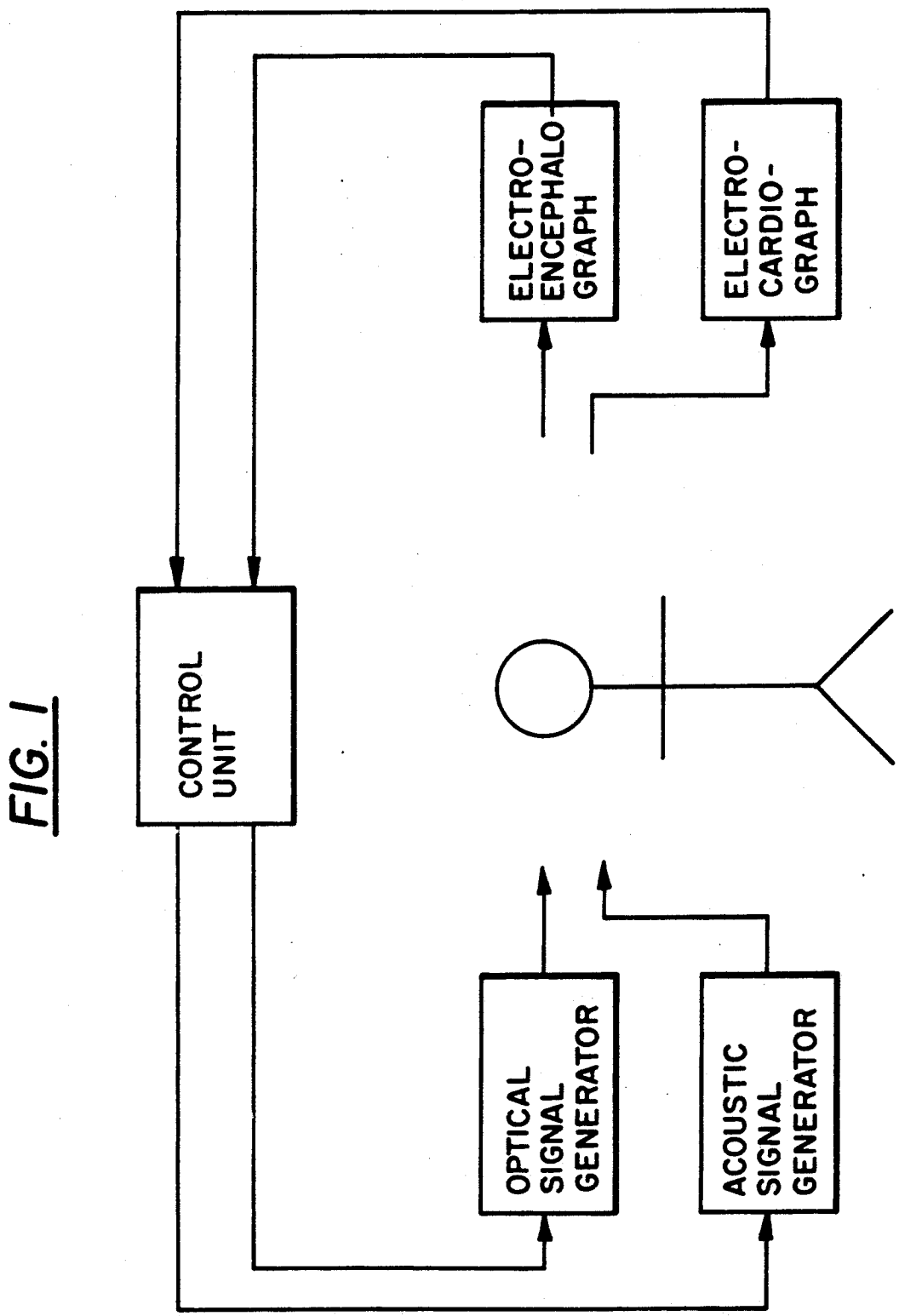
FIG. 1 illustrates a device for influencing the human body by means of acoustic, optical, mechanical and/or electric signals.

The brain is protected against undesired penetration, such as penetration by electromagnetic signals through the skull. It is, however, possible to influence the brain via the senses, preferably and probably most effectively at a subconciousness level.

The idea of influencing cerebral waves with electromagnetic waves of a slightly different frequency has not been examined.

It is not known whether there is an interaction between these slightly different frequencies and, if so, whether these frequencies converge to or diverge from each other. It is, however, conceivable to alter the form of a wave or another regular pattern to obtain an increased stimulation. A periodic stimulation is preferred, the period continuously decreasing or increasing. Such a continuous decrease or increase of the wave length or interval sooner or later implies that the "stimulation" is beyond the area, where it has any influence at all. Thus the effective time is finite and indeed very short. Moreover, the stimulation is characterised by one dominating feature during this short period, i.e. a violent, rapid change in the form and magnitude of the pattern itself towards either zero or infinity.

The question is whether it is possible to find an infinite series in such a way that the values of its elements decrease, while the series retains its character ad infinitum.

It suffices to imagine a series where the elements decrease in time, or to the right in a graphic representation. This does not limit the scope of the invention, and the specification also applies to a series, where the elements increase in time. In this case the time axis has only to be reversed.

It is indeed possible to reconcile the apparently irreconcilable: The sequence decreases continuously and still retains its character and structure ad infinitum.

This is done by a generalization of an infinite series by extending the series by elements corresponding to the existing elements in such a way that a predetermined number of the new elements, such as two, corresponds to one element of the original series. The original and the new series are superimposed in such a way that the two elements of the new series coincide with one element of the original series ad infinitum.

This is repeated for both the positive and negative direction. In the positive direction two elements of a new series of the type described above coincide with one element of the original series. In the negative direction a new series has a reverse relationship to the original series.

The question is, whether it is possible to obtain an infinite series satisfying this condition.

The solution is a "modified geometrical progression", where the successive quotients become increasingly larger and converge to one according to a predetermined rule.

The rule for elements of an infinite series satisfying the above condition is expressible by a function. The infinite series defined by said rule has the following property: Not only does a pair of elements in one series coincide with an element in the series below the first one (towards negative infinity) but the opposite also holds in the opposite direction (towards positive infinity). Moreover, for any integer N one can choose any two series so that N elements of one series coincide with an element of the other series ad infinitum and vice versa.

The elements of this infinite series are the differences between the logarithms for all pairs comprising two subsequent positive integers: $\log(p) - \log(p-1)$.

When connecting elements of an infinite series in a mutually displaced way, the following three conditions have to be satisfied:

1. Since a series is not infinite in both directions, i.e. it has a starting point (on the left-hand side) and a first element, another series starting further to the left than a given first series has to be introduced at a later element of the first series.

2. In order to avoid a sequence comprising many, especially infinitely many series giving a dense set of common points so that these points cannot be distinguished, the various series of said sequence have to be represented by different intensities at any stage of the sequence and/or have to differ in another way.

3. In order to let the sequence of pulses maintain its general character, each series has to appear with the same intensity and character at the same stage of its development as the other series at equivalent stages.

These conditions can be satisfied by letting the intensity of a part of each series increase or decrease, respectively, for instance according to a sinusoidal function, the intensities of the mutually displaced series overlapping each other and together forming a series of substantially constant pulse levels.

The pulse at each point should hardly have the properties of a sharply defined point, it should rather be diffusely increasing or decreasing. The pulses in each area of the series should form an entity, a picture or a pattern increasing or decreasing in speed depending on the direction of the series.

The principle may work with pulses resembling the ticks of a watch. The first device operated with such pulses and resulted in a noticable stimulation.

The principle is based on the fact that an organism considers such a division of time a uniform division. The organism should therefore have no access to a truely uniform division of time so that it cannot suspect or refute the uniform division.

The conditioning of the perception of time achieved by the above series in human beings can be effected by means of light, sound, vibrations, etc. The greatest stimulation is obtained by using several of these means simultaneously. The simplest and most obvious combination is sound and light, preferably light perceivable through closed eyes.

The sequence can be converted to sense pulses by transmitting said sequence to a magnetic tape, whereupon the sequence of pulses is converted to sense pulses or signals of a different type by means of a converter.

The structure of the sequence can be selected with three degrees of freedom:
1) the part of the series used (for instance starting with log 8 or log 40),
2) the starting point of a new series with respect to a preceding one (for instance at the third element), and
3) the frequency of the series.

Since the series is infinite, the intervals cannot be described by their length. It would be natural to describe the series by the first element of the series, regardless whether the element is part of the series used, i.e. log 2 − log 1 − log 2.

The device for playing the magnetic tape can be an ordinary tape recorder. Advantageously the tape is equipped with an autoreverse means, such as the autoreverse tape known from an automatic answerphone. Furthermore the tape is adjusted so that the pattern is able to continue uninterruptedly when the tape is played once more. A further advantage is that the pattern can also be played during slow reversing of the tape, so that the pattern can be used for an accelerating or decelerating stimulation, depending on the wish of the user. The autoreverse tape can for instance be a Mobius-type tape.

The most important task of the device of the invention is the decelerating stimulation of a human being, animal or robot, i.e. inducing rest, tranquility, relaxation or sleep.

Figure 2:
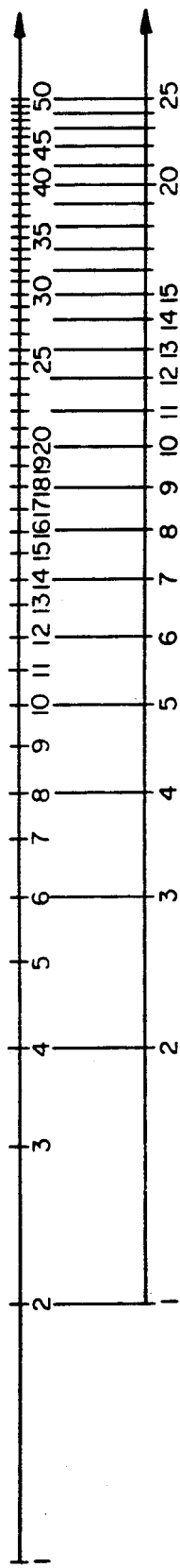
FIG. 2 illustrates an embodiment of the supplied signal.

FIG. 2 illustrates two parallel, horizontal lines, each line being divided into intervals corresponding to the difference between the logarithms of two subsequent positive integers, the division starting at the first point on the far left and progressing towards the right-hand side of the sheet. The lower line is displaced to the right with respect to the upper one, the displacement corresponding exactly to the first point indicated as 1 on the lower line being directly below point 2 on the upper line.

As is apparent from FIG. 2, any integer on the lower line corresponds ad infinitum to twice its value on the upper line. The odd numbers on the upper line do not have a corresponding integer or any other common point with the lower line.

Figure 3:
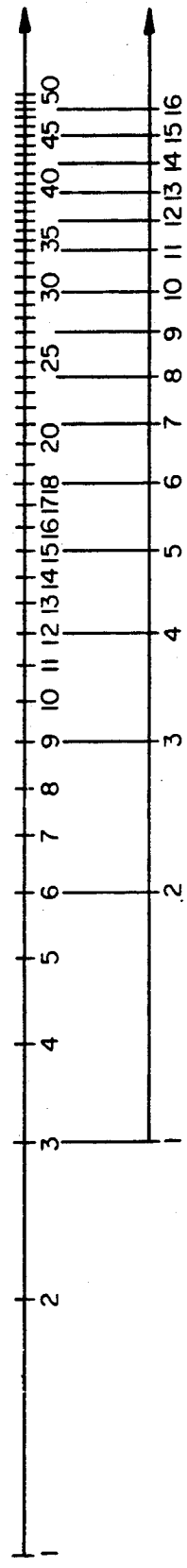
FIG. 3 illustrates another embodiment of the supplied series of pulses.

FIG. 3 corresponds to FIG. 2, with the exception that the lower line is further displaced to the right with respect to the upper one to the extent that point 1 on the lower line corresponds to point 3 on the upper line. As a result, each point on the lower line corresponds to a point on the upper line of thrice the value of the first point.

Figure 4:
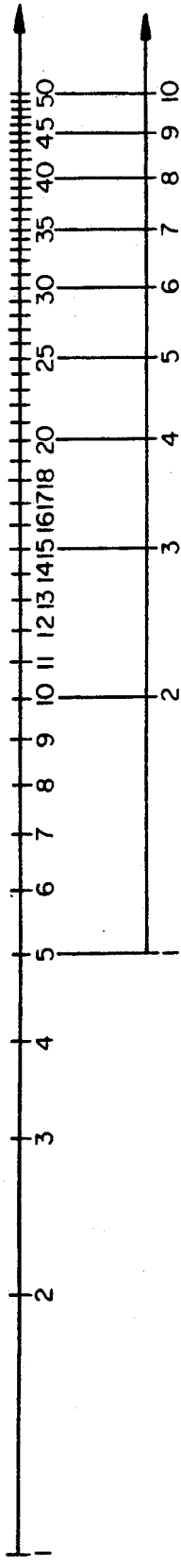
FIG. 4 illustrates a third embodiment of the supplied series of pulses.

FIG. 4 also corresponds to FIG. 2, except that the lower line is displaced so much to the right that each point on the lower line corresponds to a point on the upper line of five times its value.

Figure 5:
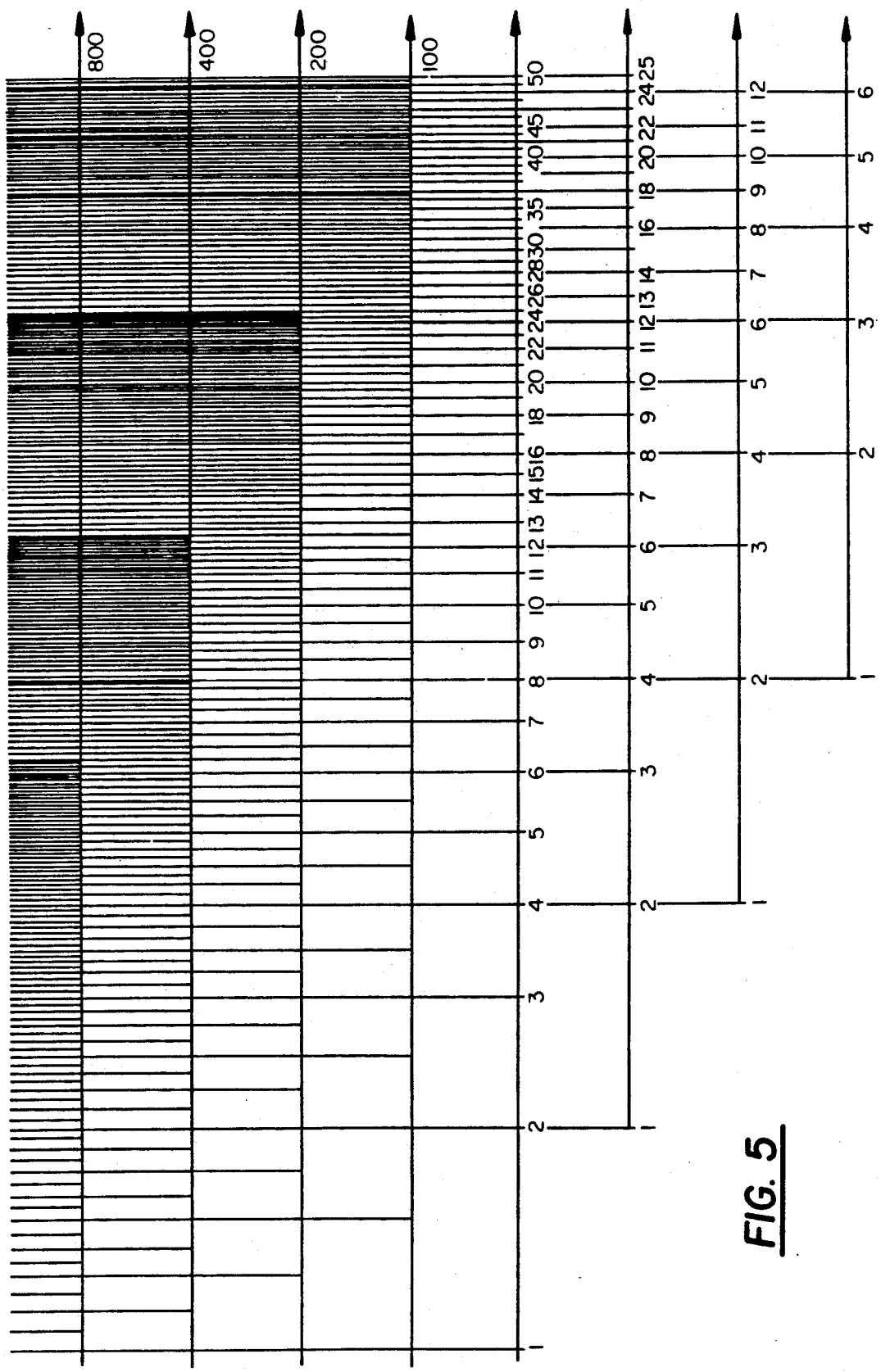
FIG. 5 illustrates an arbitrary number of series of short pulses.

FIG. 5 illustrates the same mutual displacement between a horizontal line and the line directly above, i.e. number 1 on the lower line corresponds to number 2 on the upper line. In FIG. 5, however, this relationship is repeated for several lines displaced with respect to each other. All common points on all lines are connected by vertical lines. As is apparent, the common points and the corresponding numbers correspond to each other among series in the horizontal lines.

When regarding only every second horizontal line, it is obvious that in the obtained result the factor is four, said result corresponding to the one of FIG. 5 and FIG. 2, where the factor is two, to the one of FIG. 3, where the factor is three and to the one of FIG. 4, where the factor is five.

From FIG. 5 it is moreover apparent how any number of mutually displaced uniform series can cooperate, for instance by the various series being represented by different intensities—the thickness of the lines at the common points or the like. As a result they can be separated from each other although they are superimposed and although they are converted to either sound, light or the like.

In these series the common points are situated increasingly closer to each other.

Figure 6:
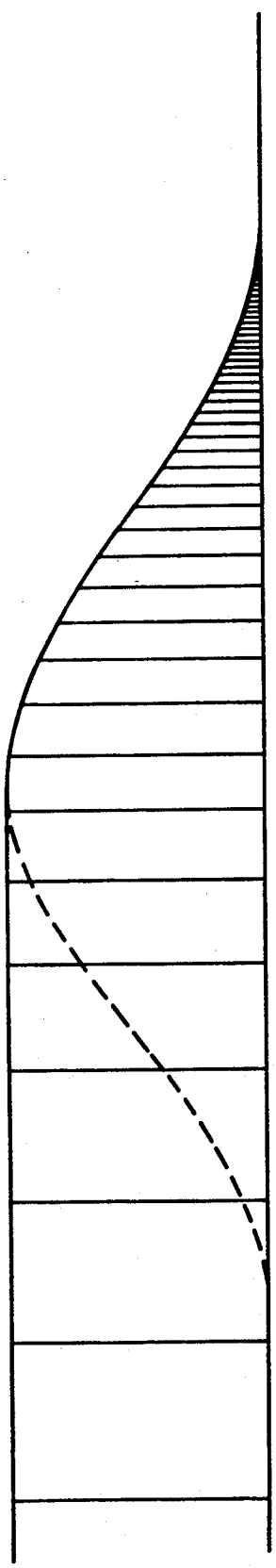
FIG. 6 illustrates how the pulses of a series can increase and decrease, respectively.

FIG. 6 illustrates how this increasing closeness can be avoided by letting series of common points increase and decrease, respectively, according to a sinusoidal function.

Figure 7:
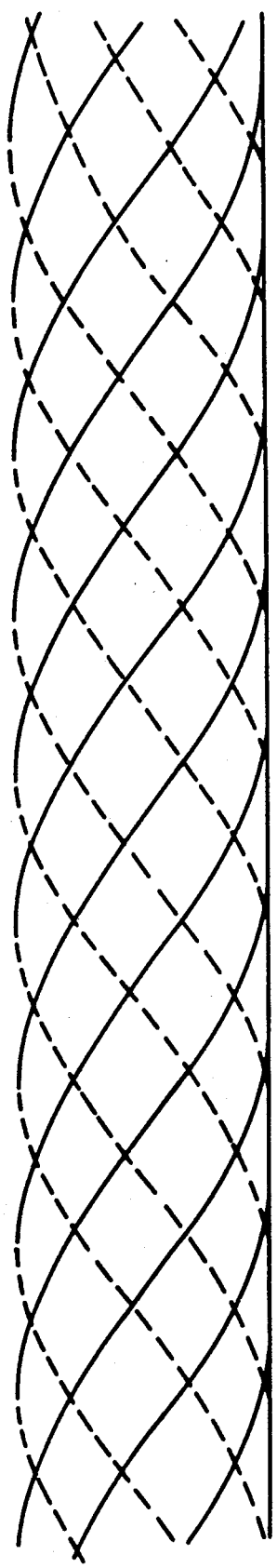
FIG. 7 shows several envelope curves.

FIG. 7 illustrates how such envelope curves for the series can overlap each other.

FIGS. 6 and 7 indicate, how the series can increase and decrease, for instance according to a sinusoidal function. It is further indicated, that an increase from the side depicting large intervals is superfluous, since the points corresponding to the pulses of such a series are already occupied by pulses of previous series, the latter to be superimposed by the first-mentioned series. When the pulses are to be added the increasing part of the sine wave or the like has to be taken into consideration, and the pulses from the two or more series in question are added. The "sum" is not necessarily an exact sum. It is sufficient to either take the highest value or take the exact sum of the values or execute a modified addition.

Figure 8:
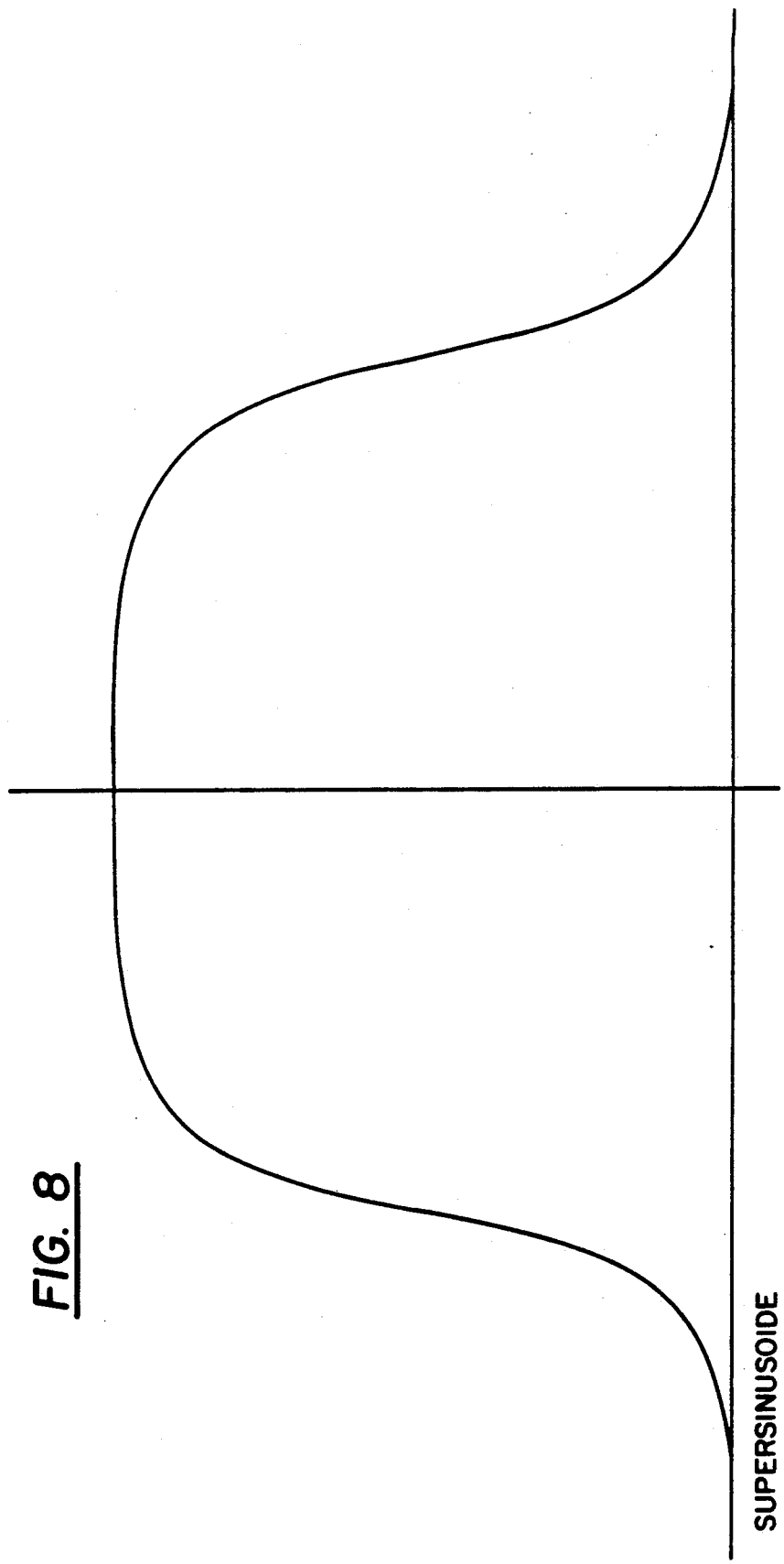
FIG. 8 shows an envelope curve in form of a super-sinusoid.

FIG. 8 illustrates an especially suitable curve, i.e. a supersinusoid derived from a supercircle and a superellipsoid.

Obviously optimal signal stimulation varies from organism to organism. In a device comprising means to detect cerebral waves the supplied pulses are advantageously controlled depending on the detected cerebral waves, cf. FIG. 1. This allows an especially extensive stimulation of the cerebral waves. The variables in this case are the envelope curves, the basis of the logarithm, the intensity, etc.

The longest perceptible—and with repetition possibly recognizable—time interval of a series, for instance log 9 to log 10, acts as an orientation point for the perception of a normal time division.

This can be avoided by submitting the entire sequence of added series to a distortion corresponding to the one described above. In this case a general scale is distorted such that n divisions of a first scale coincide with one division of a second scale when two such scales are displaced. The intensity of the pulses can be further modified in order to take the latter procedure into account.

The distortion of the scale can also be followed by a second one, etc. A double logarithm, i.e. a logarithm of a logarithm, can for instance be used.

I claim:

1. An electronic device producing light, sound or vibrational signals for influencing human beings or animals, comprising:
   means providing a plurality of series of short pulses transmitted to the person or the animal at increasing and/or decreasing intervals between the short pulses;
   means time-delaying the pulses, so that the pulses of each series are mutually time-delayed relative to corresponding pulses in respectively successive ones of said series;
   means amplitude-modulating the pulses in each series, so that increasing and decreasing envelope curves for respectively successive ones of said series overlap each other in such a manner that some of the series decrease in amplitude after a continuous steady curve, simultaneously with the remaining series increasing in amplitude according to corresponding continuous steady curves.

2. The device of claim 1 wherein:
   said modulating means provide that the increasing and decreasing curves succeed each other so that transitions from each preceding series to each respective succeeding series is not noticeable to a human being subjected to the pulses.

3. The device of claim 1, wherein:
   said modulating means provide that the pulses of each series increase and/or decrease according to a sinusoidal function.

4. The device of claim 1, wherein:
   said continuous steady curve is logarithmic.

5. A magnetic recording tape to be played on a magnetic tape player, comprising: a tape carrying a magnetic recording medium on which a plurality of series of short pulses have been recorded at increasing and/or decreasing intervals between the short pulses, the pulses of each series being mutually time-delayed relative to corresponding pulses in respectively successive ones of said series, and the short pulses of each series being amplitude-modulated whereby increasing and decreasing envelope curves for respectively successive ones of said series overlap each other in such a manner that respective preceding series decrease in amplitude after a continuous steady curve, simultaneously with respective following series increasing in amplitude according to corresponding continuous steady curves.

6. The magnetic recording tape of claim 5, wherein: said continuous steady curve is sinusoidal.

7. The magnetic recording tape of claim 5, wherein: said continuous steady curve is logarithmic.

* * * * *